United States Patent
Paris et al.

(10) Patent No.: US 8,419,426 B2
(45) Date of Patent: Apr. 16, 2013

(54) DEVICE FOR POSITIONING AND IMMOBILIZING A SURGICAL GUIDE IN A PATIENT'S MOUTH

(75) Inventors: Marion Paris, Lyons (FR); Thomas Fortin, Sleymieu (FR)

(73) Assignee: Hospices Civils de Lyon, Lyon Cedex (FR)

( * ) Notice: Subject to any disclaimer, the term of this patent is extended or adjusted under 35 U.S.C. 154(b) by 169 days.

(21) Appl. No.: 12/670,177

(22) PCT Filed: Jul. 22, 2008

(86) PCT No.: PCT/FR2008/051378
§ 371 (c)(1),
(2), (4) Date: Jun. 21, 2010

(87) PCT Pub. No.: WO2009/016312
PCT Pub. Date: Feb. 5, 2009

(65) Prior Publication Data
US 2010/0291504 A1    Nov. 18, 2010

(30) Foreign Application Priority Data
Jul. 23, 2007 (FR) .................................... 07 56670

(51) Int. Cl.
*A61C 3/00* (2006.01)
(52) U.S. Cl.
USPC .......................................................... 433/75
(58) Field of Classification Search ............. 433/72–75, 433/215–218, 136–140, 93; 128/846, 857–862; 606/96
See application file for complete search history.

(56) References Cited

U.S. PATENT DOCUMENTS

| | | | | |
|---|---|---|---|---|
| 4,889,490 A | * | 12/1989 | Jenkinson | 433/136 |
| 4,968,250 A | * | 11/1990 | Small | 433/173 |
| 4,969,473 A | * | 11/1990 | Bothwell | 128/858 |
| 5,370,117 A | | 12/1994 | McLaurin, Jr. | |
| 7,024,237 B1 | | 4/2006 | Bova et al. | |
| 2005/0045187 A1 | | 3/2005 | Huttner | |
| 2006/0019216 A1 | * | 1/2006 | Priluck et al. | 433/140 |

FOREIGN PATENT DOCUMENTS

| | | |
|---|---|---|
| DE | 4339049 A1 | 5/1995 |
| DE | 10036027 A1 | 1/2002 |
| DE | 10049938 A1 | 5/2002 |
| EP | 0574868 A2 | 12/1993 |
| EP | 0979057 A1 | 2/2000 |
| WO | 94/26199 A1 | 11/1994 |

* cited by examiner

*Primary Examiner* — Yogesh Patel
(74) *Attorney, Agent, or Firm* — Clark & Brody

(57) ABSTRACT

The invention relates to a positioning and immobilization device for positioning and immobilizing a mandibular or maxillary surgical guide on a patient, which guide is adapted to preparing for and to fitting at least one dental implant and is provided with a link slab member designed to extend outside the oral cavity when the surgical guide is placed in register with the patient's mandible or maxilla, said positioning and immobilization device being characterized in that it comprises a body that has bearing face for bearing against the outside of the head of the patient, and a fastener designed to co-operate with the link slab member of the surgical guide.

9 Claims, 4 Drawing Sheets

DEVICE FOR POSITIONING AND IMMOBILIZING A SURGICAL GUIDE IN A PATIENT'S MOUTH

The present invention relates to the technical field of surgical guides used for putting dental implants into place.

Patent Applications WO94/26199 and EP0979057 propose surgical guides that are particularly adapted to positioning dental implants with great accuracy. The surgical guides proposed by those documents are more particularly adapted to performing the positioning in a plurality of steps. One of the steps, performed after the body of the guide has been formed on the basis of an impression of the maxilla or of the mandible of the patient who is to receive the prostheses, consists in scanning the maxillas of the patient while the body of the guide is in position. A following step consists, on the basis of the information from the scanner and from the guide, in putting guide tubes into place in the body of the guide for the purpose of guiding the drilling that is performed by means of an automated drilling center. Once fabrication of the surgical guide is finished in this way, said surgical guide is positioned on the maxilla or on the mandible of the patient and is immobilized by means of intra-osseous anchor screws so as to enable the surgeon to perform the pre-implant drilling in the bone of the maxilla or of the mandible without any risk of the surgical guide being displaced in untimely manner.

Such surgical guides and the ways in which they are used are fully adapted to being used on healthy patients whose mucous membranes have not undergone any particular alteration. Radiotherapy and resection or reconstruction surgery degrades the physiognomy of soft tissue and reduces its potential for wound-healing. In patients suffering from upper aerodigestive tract cancer, the mucous membranes are degraded, the potential for wound-healing is reduced and there exists a life-threatening risk that osteo-radio-necrosis might be caused by invasive surgery. In that type of patient, it is necessary to preserve the blood supply to the bone and thus to preserve the periosteum, and to reduce the gateways through which infection can pass. It is therefore not possible to immobilize surgical guides by anchoring them with intra-osseous screws.

Devices are also known that are described, for example, in Documents DE 100 49 938, DE 100 36 027, or indeed EP 0 574 868 A2, that make it possible to perform the positioning and/or to compute physiological parameters with a view to preparing for dental implants and to putting them into place. Those devices include various rigid stabilizer systems on the head of a patient. Unfortunately, in addition to being impractical and difficult for the surgeon to use, those systems often do not make it possible to obtain genuine stability for the surgical guides and/or measurement means on the patient. In addition, such devices are no more adapted to treating patients suffering from upper aerodigestive tract cancer than the above-mentioned surgical guides.

The need has therefore arisen for means that enable surgical guides to be used on such patients while reducing the invasiveness of the surgical action at the implantation zones, and while retaining the high implantation accuracy offered by putting the surgical guides into place.

In order to achieve these objects, the invention provides a positioning and immobilization device for positioning and immobilizing a mandibular or maxillary surgical guide on a patient, which guide is adapted to preparing for and to fitting at least one dental implant, said positioning and immobilization device being characterized in that it comprises:

a body forming a mask having a bearing face adapted to fit over at least a portion of the patient's face with the patient being in a mouth-open position;

fastener means for fastening a surgical guide to the body; and a link member co-operating with the fastener means and with the surgical guide to immobilize the surgical guide on the mandible or the maxilla of the patient with the mouth open, and extending from the surgical guide outside the oral cavity when the surgical guide is placed in register with the patient's mandible or maxilla.

By means of the body, use of such a positioning and immobilization device makes it possible to procure stable bearing against the head of the patent, thereby, in view of the link between the surgical guide and the body, guaranteeing that the surgical guide is positioned and immobilized in position on the mandible or on the maxilla of the patient without it being necessary to use immobilization screws engaged through the gum and into abutment against the bone. The congruence between the bearing face and at least a portion of the patient's face offers great accuracy for the positioning and very good immobilization of the device. The positioning and immobilization device of the invention thus makes it possible to reduce the mucous-membrane and bone lesions to no more than the drilling for putting the implants into place. The idea is thus to perform minimally invasive surgery.

According to a characteristic of the invention that makes it possible to optimize the reliability of the positioning, the fastener means are adapted to provide a rigid link between the body and the surgical guide.

With the same aim, and according to another characteristic of the invention, the fastener means are adapted to provide a separable rigid link between the body and the surgical guide. The separable nature of this link makes it easier to put the resulting assembly into place, by allowing the body of the positioning and immobilization device to be put into place initially, and then allowing the surgical guide to be fitted in position on the patient's mandible or maxilla.

In accordance with the invention, the fastener means of the positioning device that are designed to co-operate with the link member of the surgical guide may be implemented in any manner suitable for guaranteeing satisfactory positioning accuracy. According to a characteristic of the invention that aims to make it easy to assemble the surgical guide and the positioning and immobilization device, the fastener means comprise a housing for receiving the link member, which housing has a shape complementary to the shape of said link member that extends from the surgical guide outside the oral cavity.

In a preferred but not strictly necessary embodiment, the link member is adapted to fit into the housing.

In addition, the link member may be integral with or separably secured to the surgical guide.

In order to optimize the effectiveness of the immobilization, the bearing face is preferably, but not necessarily, adapted to fit over a portion of the nose, of the forehead, of the cheekbones, of the chin, and of the mandibular angles of the patient. By fitting over these regions that have accentuated relief, the bearing face contributes to immobilizing the body effectively by exerting pressure that is well distributed over the surface of the patient's face, thereby contributing to the patient's comfort and reducing the discomfort caused by putting the positioning and immobilization device of the invention into place.

Also with the same aim and according to another characteristic of the invention, the bearing face is adapted to fit over the patient's entire face substantially to the hairline, to the chin, and to the gonial angles when the patient is in a mouth-open position.

According to a characteristic of the invention aiming to increase the patient's comfort, the body is provided with ocular openings and with an oro-nasal opening, which openings are designed to be placed in register respectively with the eyes, and with the mouth and the nostrils of the patient.

In a preferred embodiment, in order to increase the stability of the positioning and immobilization device of the invention, the body forms a mask fitting over at least a portion of the face of the patient.

According to another characteristic of the invention, the positioning device further comprises clamping means designed to come to bear against the rear portion of the patient's head so as to press the bearing means against the patient's face. Such clamping means may be implemented in any suitable manner and, for example, be constituted by a strap that passes behind the head and that has its ends fastened to the body of the positioning and immobilization device.

In a preferred embodiment of the positioning and immobilization device, the body is made of a thermoplastic material having a softening temperature lying in the range 38° C. to 80° C., and preferably in the range 40° C. to 50° C. This preferred embodiment is particularly adapted to fabricating the body of the device by molding said body directly over the patient's face.

The invention also provides a set or a kit for preparing at least one positioning and immobilization device of the invention by molding the body of the device directly over the head of the patient. Such a set or kit then comprises:

at least one plate that is made of a thermoplastic material having a softening temperature lying in the range 38° C. to 80° C. and, preferably, in the range 40° C. to 50° C., and that is designed to form the body of the positioning device;

a link member for linking a surgical guide to the body of the positioning device once the plate has been shaped; and fastener means designed to co-operate with the link means of the surgical guide.

According to a characteristic of the invention, the plate is provided with at least two pre-cut ocular windows that are designed to be placed in register with the patient's eyes, and said plate is also provided with a pre-cut oro-nasal window that is designed to be placed in register with the patient's mouth and nostrils. In a preferred embodiment, the plate then has a substantially oval shape.

The invention also provides a jig for fitting at least one dental implant in a patient, which jig comprises:

a mandibular or maxillary surgical guide; and a device for positioning and immobilizing the surgical guide on the patient.

According to a characteristic of the jig of the invention, the surgical guide and the link member of the positioning device are integral with or separably secured to each other.

Also according to the invention, the link member and the fastener means of the positioning device co-operate with each other removably.

The invention also provides a method of fabricating a positioning and immobilization device of the invention, which method comprises a step of molding the body of the device to the shape of the patient's face with the patient in a mouth-open position.

Naturally, the various above-mentioned characteristics of the invention may be implemented together in different combinations when they are not mutually incompatible or mutually exclusive.

In addition, various other characteristics of the invention appear from the following description given with reference to the accompanying drawings which, by way of non-limiting example, show an embodiment of the invention, and in which.

Figure 1:
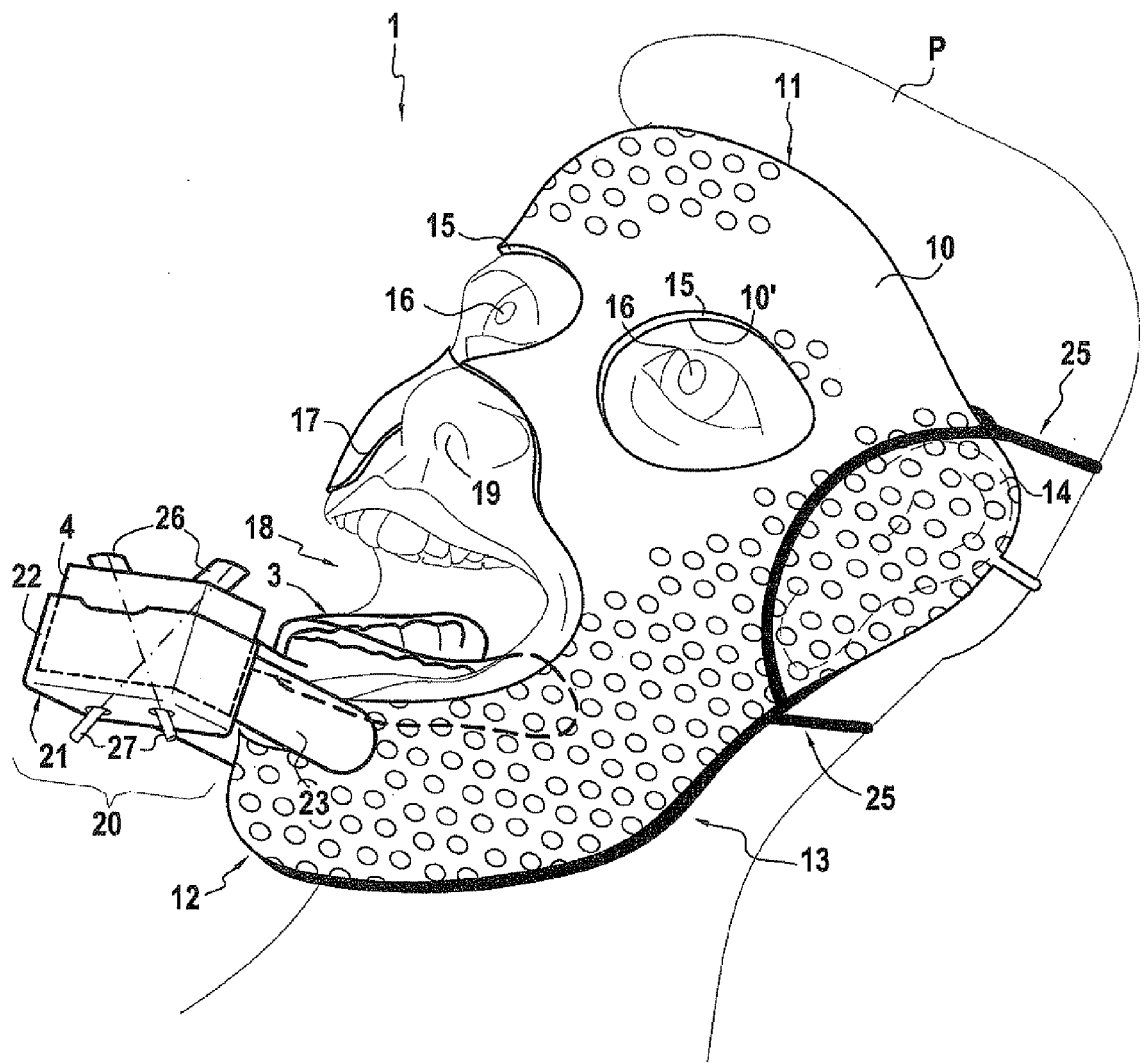
FIG. 1 is a diagrammatic view of the positioning and immobilization device of the invention as placed on a patient's head.

An object of the present invention is to propose a positioning and immobilization device, as shown in FIG. 1 and designated overall by reference 1, which device is designed to facilitate fitting dental implants that are designed to hold dental prostheses.

The problem with fitting dental implants lies in how to position the implants accurately in regions of the maxilla and of the mandible that offer sufficient amounts of bone to guarantee stability for the implant as well as lasting anchoring therefor. In order to guarantee optimum positioning, a process is implemented for determining the positions of the implants and for putting them into place, such as, for example, a process as described in Applications WO 94/26 199 and EP 979 057.

A first step consists in forming an impression of the jaw that is to receive the prostheses by using an impression material such as silicone, an alginate, a hydrocolloid, or any other material used for this purpose. The impression is then used to make a plaster model or cast of the jaw that is to receive the prostheses.

Figure 2:
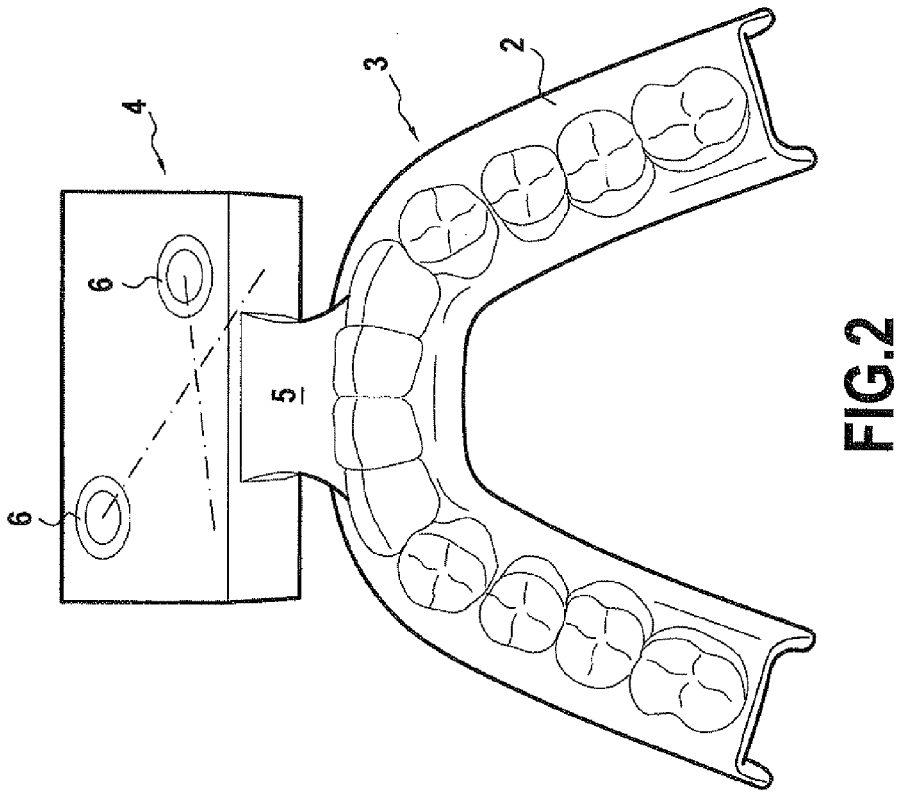
FIG. 2 is a diagrammatic view of a surgical guide, before guide tubes are put into place, that is designed to be associated with the positioning and immobilization device as shown in FIG. 1.

A second step consists in using the plaster model as a basis for fabricating a test prosthesis that is positioned in the mouth of the patient, so as to check that it matches exactly the morphology of the patient. Once the shape of the test prosthesis has been finalized and validated, it is used as a basis for fabricating the resin body 2 of a surgical guide 3 that is shown in FIG. 2. In order to enable the body of the surgical guide to be seen by a scanner in a subsequent step, the body of the surgical guide is fabricated using a radio-opaque resin such as the resin sold under the name SR Vivo TAC/SR Ortho TAC by Ivoclar Vivadent located in Saint Jorioz in France. As in a known method and in order to allow the surgical guide to be handled subsequently by a machining robot, link means 4 are fastened to the body 2 in such a manner as to find themselves outside the oral cavity when the surgical guide 3 is placed inside said oral cavity. In the example shown, a prefabricated slab is used as the link means 4, which slab is made of an acrylic resin such as, for example, the resin sold under the name X-cube by Keystone Inc. located in Burlington, Mass., USA. The slab 4 is then linked to the body 2 by an arm made of resin 5, so as to leave sufficient space for the lip between the body 2 and the slab. Thus, the length of the arm 5, as measured between the slab 4 and the body 2, has a value lying in the range 25 mm to 35 mm. A known characteristic of the X-cube slab is that it has two tubes 6 that are made of a radio-opaque material such as titanium, and whose axes lie in respective ones of two parallel planes and extend at 90° relative to each other. The two tubes 6 are designed firstly to enable the link slab 4 to be identified by the scanner, and secondly to allow the surgical guide to be fastened rigidly to the bed of a machining robot. Thus, the link slab 4 and its tubes 6 form a fiduciary marker. Naturally, any suitable link means other than the X-cube could be used.

In this example, the test prosthesis and the surgical guide are designed for equipping the mandible of a patient with prostheses. Naturally, a test prosthesis and a surgical guide could be fabricated in the same way for the maxilla of a patient.

Figure 3:
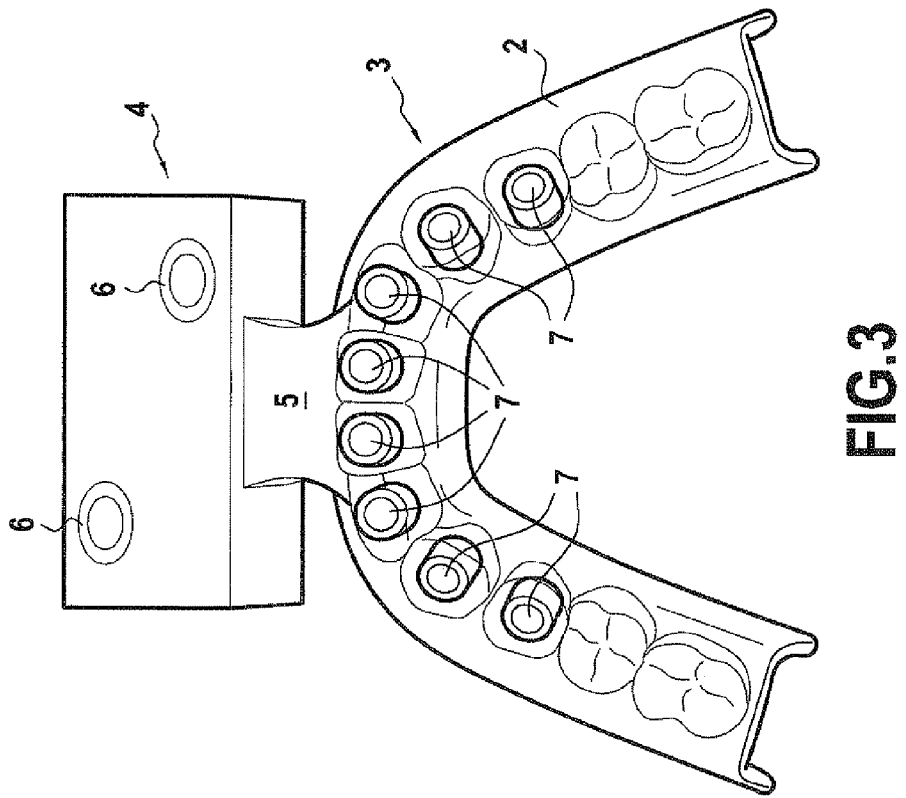
FIG. 3 is a diagrammatic view of the surgical guide as shown in FIG. 2 after guide tubes have been put into place.

The next step consists in performing an X-ray examination of the patient's mandible with the surgical guide, as fabricated previously, in place so as to determine the best possible locations for the implants as a function of the state and of the distribution of the bone mass of the patient and as a function of the planned locations of the prostheses. The X-ray examination, generally performed using a scanner, makes it possible for a computer to plan the implantation of the implants, e.g. by using the software CADImplant sold by Keystone. The electronic file of this planning is then used by a machining robot to place guide tubes 7 in the body of the surgical guide, as shown in FIG. 3. The link slab 4, which is visible during the X-ray examination, is used for fastening the surgical guide 3 to the bed of the machining robot. This then defines a reference that is common to the machining and to the planning, and thus makes it possible for the axes of the implants to coincide exactly with the axes of the guide tubes 5 in compliance with the planned implantation.

Once the machining guide 3 has been provided with its tubes 5 fabricated in this way, it is put back into the patient's mouth and, in the example shown, at the patient's mandible. The surgeon can then drill pre-implantation bores by following the tubes 7. In order to preserve the full advantage of the accuracy obtained by the same use of the surgical guide 3 with these link means 4, of the X-ray examination, of the planning by computer, and of the machining robot, it is necessary for the surgical guide, after it has been machined, to be re-positioned very accurately at the location that it was in during the X-ray examination, in a manner such that, by following the drilling guides, the surgeon is sure to form the implantation orifices as planned.

In order to achieve this accuracy objective, the invention proposes to use the positioning and immobilization device 1 firstly during the X-ray examination and secondly during the surgical operation, so as to offer a surgical guide positioning reference that is common to these two steps of the process for putting the implants into place.

To this end, and as shown more particularly in FIG. 1, the positioning and immobilization device 1 comprises a body 10 that comes to bear against the head of the patient P. In the example shown, by way of bearing means for bearing against the outside of the head of the patient, the body 10 is provided with a bearing face 10' that is situated under the body 10 and that has a shape complementary to the shape of the face of the patient P. In this example, the body 10 is more particularly implemented in the form of a mask that fits over almost the entire face of the patient P by extending from the hairline 11 to the chin 12 and to the gonial angles 13 or angles of the mandible. It can be observed that the body 10 also fits over the ears 14 of the patient P, although it is also possible for the body 10 to have recesses at the ears 14, so as to leave the ears uncovered. In order to guarantee a certain level of comfort for the Patient P, the body 10 is provided with two ocular windows 15 placed to be in register with the eyes 16 of the patient P. The body 10 is also provided with an oro-nasal window 17 placed to be in register with the mouth 18 and with the nostrils 19 so as to enable the patient to breath normally through the nostrils. It should be noted that the body 10 is adapted to fit over the patient's face in a position in which the mouth 18 is open wide enough to enable the surgeon to work inside said mouth, the body 10 being in a position, in particular, to enable the surgical guide 3 to be inserted and removed.

In order to enable the body 10 and the surgical guide 3 to be assembled together, the positioning and immobilization device 1 is further provided with fastener means 20 designed to co-operate with the link means 4 of the surgical guide 3. In the example shown, the fastener means 20 are adapted to form a rigid link between the body 10 and the surgical guide 3. To this end, the fastener means 20 comprise a box 21 that defines a housing 22 for receiving the link means 4, which housing is of shape complementary to the shape of said link means 4 and thus, in the example shown, of substantially rectangular block shape. The housing 22 is open at its top so as to enable the slab constituting the link means 4 to be engaged or fitted into said housing. The housing 21 is also linked to the body 10 by one or more rigid arms 23.

The positioning and immobilization device 1 of the invention as constituted in this way is used, in the above-described process, in the following manner.

Prior to the X-ray examination, the positioning and immobilization device 1 is placed over the face of the patient P while being pressed fully against said face by clamping means 25, such as, for example, optionally elastic flexible ties connected to the body 10 and going around the back of the patient's skull as shown in FIG. 1. Then, the surgical guide or the blank thereof, as shown in FIG. 2 is put into place in register with the mandible of the patient. The link means 4 then co-operate with the fastener means 20 by being engaged in the housing 22 defined by the box 21. In order to prevent any untimely movement of the link means 4, locking rods 26 are engaged through the tubes 6 until they project out though locking bores 27 provided in the bottom of the box 21.

The patient equipped in this way can then be given the X-ray examination necessary for planning the implantation. At the end of this X-ray examination, the surgical guide 3 is removed and the positioning and immobilization device 1 is removed from the face of the patient.

Then, the implantation is planned and the machining of the surgical guide 3 is machined as explained above.

Figure 4:
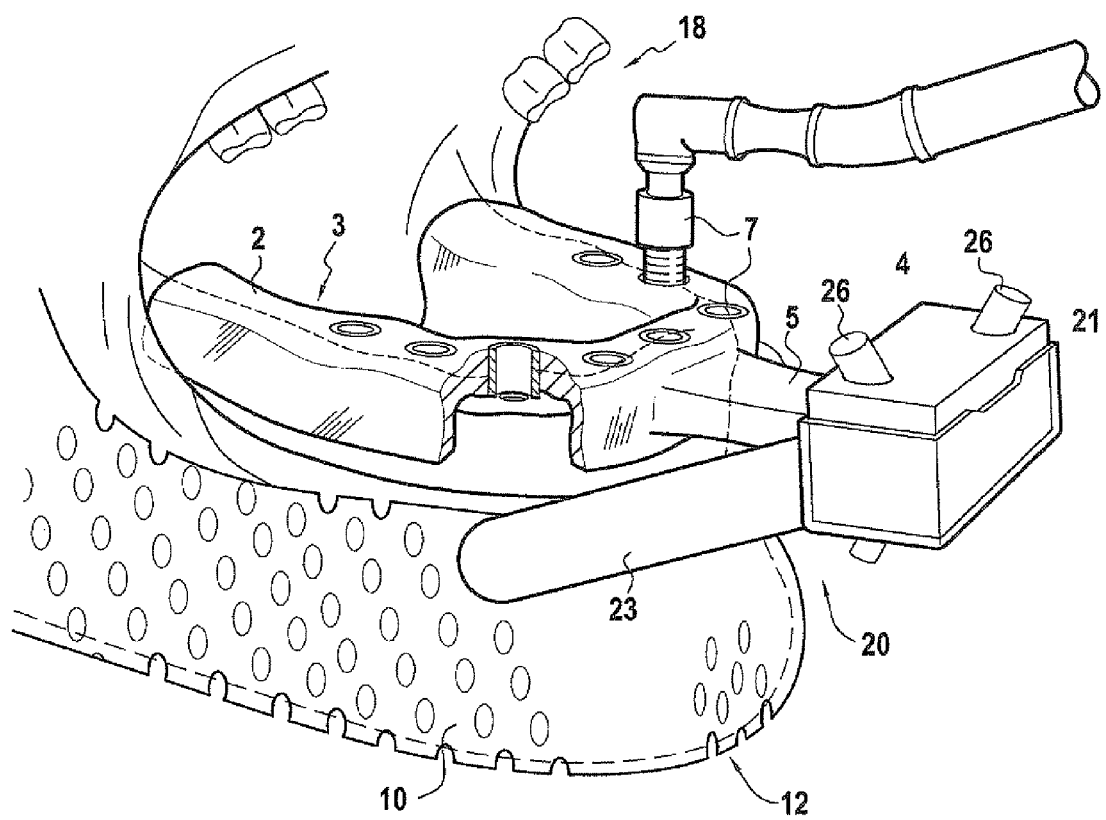
FIG. 4 is a diagrammatic view showing how the positioning and immobilization device shown in FIG. 1 is used in the context of an implantation surgical operation in association with the surgical guide shown in FIG. 3.

For the implantation stage, the positioning and immobilization device 1 is, once again, placed over the patient's face. The surgical guide 3, as shown in FIG. 3, is, once again, placed in the patient's mouth in register with the patient's mandible, the link means 4 being engaged in the fastener means while being locked therein by the rods 26. The surgeon can then perform the drilling while being guided by the tubes 7, as shown in FIG. 4, during an operation conducted under general anesthetic, for example.

The immobilization and fastening device 1 of the invention thus makes it possible to guarantee very good matching between the position of the surgical guide during the X-ray examination and the position of the same surgical guide during the surgical action itself.

In the example shown, the link means 4 are locked relative to the fastener means 20 by means of the rods 26. However, any other locking means making it possible to prevent any relative movement between the link means and the fastener means may be considered.

The positioning and immobilization device 1 of the invention may be fabricated in different ways.

Figure 5:
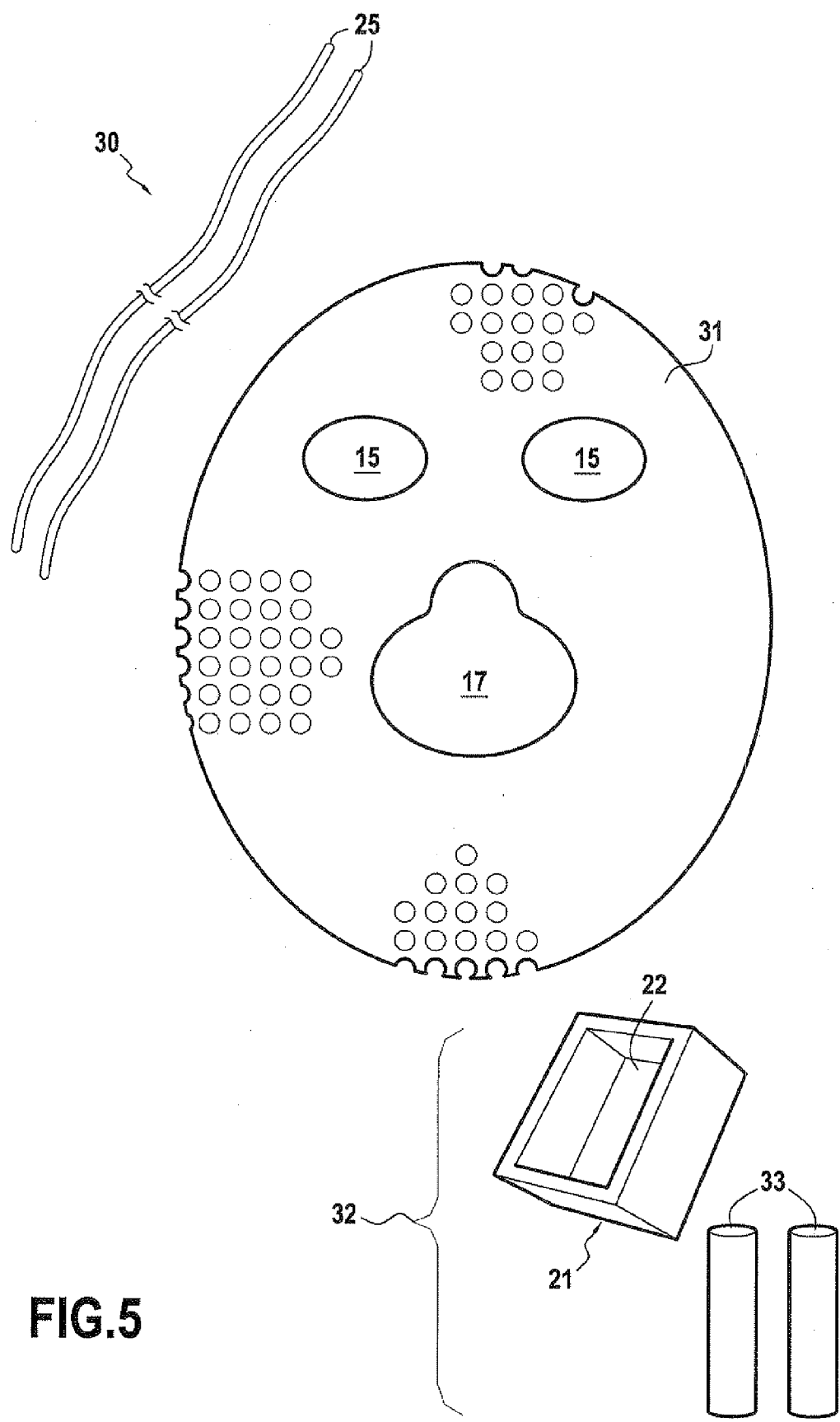
FIG. 5 is a diagrammatic view of a set of elements or of a kit designed to enable the positioning and immobilization device as shown in FIG. 1 to be fabricated.

In a preferred embodiment, the device 1 is fabricated to measure for each patient. To this end, a set or kit is used as shown in FIG. 5 and designated overall by the reference 30, which set or kit includes a plate 31 made of a thermoplastic material having a softening temperature lying in the range 38° C. to 80° C. and, preferably, in the range 40° C. to 50°. For example, the plate 30 is made of a low-temperature thermoplastic material that is sold under the name Posicast-lite by Sinmed BV located in Reeuwijk in the Netherlands. The plate 31 that, in the example shown, has a substantially oval shape and that is designed to form the body of the positioning device 1, has two ocular windows 15 that are pre-cut and an oro-nasal window 17 that is also pre-cut. The set 30 also includes elements 32 for making up the fastener means 20 that are designed to co-operate with the link means 4 of the surgical guide 3. In the example shown, the elements 32 comprise firstly the box 21 that defines the housing 22 for receiving the slab 4, and secondly two blocks or cylinders of resin that are designed to enable the box 21 to be fastened rigidly to the body or mask 10, as appears below. The set 30 finally includes elastic ties 25 that are designed to constitute the means for clamping the device to the head of the patient P.

The device 1 is fabricated before the X-ray examination is conducted and after the surgical guide 3 or the blank thereof, as shown in FIG. 2, has been fabricated.

A first step of this fabrication consists in molding the plate 31 over the face of the patient in a mouth-open position. For this purpose, the plate 31 is plunged for about one minute into a bath of hot water at 70° C. The plate 31 is then dried between two towels that absorb the excess water and bring the plate back down to a temperature of about 45° C., at which the plate 31 is in a softened or plastic state and can be applied to the face of the patient so as to match the shapes of said face exactly. Naturally, during this molding, the plate 31 is placed in such a manner that the ocular windows 15 are placed at the eyes of the patient and the oro-nasal window is placed in register with the nostrils and with the open mouth of the patient. Once this molding has been performed, the plate 31 is left to cool on the face of the patient and it then forms the body 10 of the device 1. It should be noted that the plate 31 may advantageously be molded by two operators working simultaneously.

Once the body 10 has cooled and has recovered its rigidity, it can be removed from the patient's face and can be the subject of finishing operations aimed in particular at removing any sharp edges that might injure the patient. The elastic ties 25 are then fastened back to the body 10 that is put back over the face of the patient in order to put the fastener means 20 into place. For this purpose, the box 21 is fitted to the link means 4 of the surgical guide 3 and is locked by the rods 26. Then, the surgical guide 3 is placed in the patient's mouth in register with the patient's mandible in a position corresponding to the optimum positions of the prostheses that are to equip the mandible. The box 21 is then fastened rigidly to the front portion of the body 10 by means of the cylinders 33 and/or of an adhesive resin, such as, for example, the resin sold under the name Unifast Trad by GC France located in Bonneuil sur Marne in France.

After the resin has been cured, i.e. polymerized, the fabrication of the positioning and immobilization device 1 of the invention is complete, and the X-ray examination can be conducted. It should be noted that the X-ray examination may be conducted either immediately after completion of the fabrication of the device 1, or later, insofar as, in order to remove the device 1, it suffices to unlock the link between the surgical guide 3 and the device 1 by removing the rods 26, and then to remove the surgical guide 3 and finally the device 1. It should also be noted that the rigidity of the body 10 makes it possible to put it back into place and to remove it again as many times as necessary while also, once the link between the surgical guide 3 and the device 1 has been locked, guaranteeing that the surgical guide 3 is in the same position as the position it occupied while the positioning and immobilization device 1 was being fabricated. It is this position that will be taken up again for the X-ray examination and for the surgical operation, once the fabrication of the surgical guide 3 is complete, as explained above.

Naturally, the positioning and immobilization device 1 of the invention may be fabricated in any other manner insofar as it is fabricated in such a manner as to guarantee that the surgical guide 3 finds itself in an identical position each time the assembly is put in place over the patient's face.

Furthermore, in the above-described example, the surgical guide includes guide tubes 7. However, each of said guide tubes may be replaced merely by a respective bore formed directly in the surgical guide.

Thus, various modifications may be made to the invention within the ambit of the claims.

The invention claimed is:

1. A positioning and immobilization device for positioning and immobilizing a mandibular or maxillary surgical guide on a patient, said guide is adapted to fit a dental implant, said positioning and immobilization device comprising:
    a body comprising a rigid mask having a bearing face adapted to fit over the patient's entire face, the body being provided with ocular openings and with an oro-nasal opening, said openings are designed to be placed in register, respectively, with the eyes, and with the mouth and the nostrils of the patient; the body being made of a thermoplastic material having a softening temperature lying in the range of 38° C. to 80° C.;
    a fastener device adapted to provide a rigid link between the body and a surgical guide, the fastener device comprising a box that defines a housing having an open top and linked to the body by a rigid arm, and a link slab member having a shape complementary to a shape of said housing and adapted to fit into the housing for co-operating with the fastener device and with the surgical guide to immobilize the surgical guide on the mandible or the maxilla of the patient with the mouth open, and extending from the surgical guide outside the oral cavity when the surgical guide is placed in register with the patient's mandible or maxilla.

2. The positioning and immobilization device according to claim 1, characterized in that the fastener device is adapted to provide a separable rigid link between the body and the surgical guide.

3. The positioning and immobilization device according to claim 1, characterized in that the bearing face is adapted to fit over a portion of a nose, forehead, cheeks, chin, and mandibular angles of the patient.

4. The positioning and immobilization device according to claim 1, further comprises clamping member designed to come to bear against a rear portion of the patient's head so as to press the bearing face against the patient's face.

5. The positioning and immobilization device of claim 1, wherein the softening temperature is in the range of 40° C. to 50° C.

6. A jig for fitting a dental implant in a patient, said jig comprises: a mandibular or maxillary surgical guide; and the positioning and immobilization device according to claim 1.

7. The jig according to claim 6, characterized in that the surgical guide and the link slab member of the positioning device are integral with or separably secured to each other.

8. The jig according to claim 6, characterized in that the link member and the fastener device of the positioning device co-operate with each other removably.

9. A method of fabricating a positioning and immobilization device according to claim 1, said method comprises a step of molding the body of the device to a shape of the patient's face with the patient in a mouth-open position.

\* \* \* \* \*

UNITED STATES PATENT AND TRADEMARK OFFICE
CERTIFICATE OF CORRECTION

PATENT NO. : 8,419,426 B2  Page 1 of 1
APPLICATION NO. : 12/670177
DATED : April 16, 2013
INVENTOR(S) : Paris et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this
First Day of September, 2015

Michelle K. Lee
*Director of the United States Patent and Trademark Office*